(12) United States Patent
Maass

(10) Patent No.: US 7,408,704 B2
(45) Date of Patent: Aug. 5, 2008

(54) DEVICE FOR OPTICALLY CONTROLLED MICRO-MANIPULATION OF BIOLOGICAL SPECIMENS

(75) Inventor: Andreas Maass, Hamburg (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 11/441,715

(22) Filed: May 25, 2006

(65) Prior Publication Data

US 2006/0274406 A1 Dec. 7, 2006

Related U.S. Application Data

(63) Continuation of application No. 10/484,913, filed on Jan. 26, 2004, now abandoned.

(30) Foreign Application Priority Data

Jul. 27, 2001 (DE) ............................... 101 36 572
Jul. 18, 2002 (EP) ..................... PCT/EP02/07979

(51) Int. Cl.
*G02B 21/00* (2006.01)

(52) U.S. Cl. ..................... 359/368; 359/392; 435/30; 700/58

(58) Field of Classification Search .......... 359/368–398
See application file for complete search history.

(56) References Cited

U.S. PATENT DOCUMENTS 4,749,270 A * 6/1988 Endo et al. .................. 359/392
4,907,158 A * 3/1990 Kettler et al. ................. 700/58
4,920,053 A * 4/1990 Inoue et al. .................... 435/30
5,114,854 A * 5/1992 Bertholdt ....................... 435/30
5,677,709 A * 10/1997 Miura et al. ................. 345/161
6,159,199 A  12/2000 Syska et al. ...................... 606/1
2003/0021017 A1* 1/2003 Eijsackers et al. ........... 359/368

FOREIGN PATENT DOCUMENTS

DE   197 40 324 A1   3/1999
JP      9211338 A    8/1997

OTHER PUBLICATIONS

Leica AS TP Microscope information (online) www.llight-microscopy.com, Retrived from web.archive.org, (http://web.archive.org/web/*/http://www.light-microscopy.com) Jun. 1, 2002 version, 7 pages.*
English Abstract of the Reference DE 197 40 324 A1.

* cited by examiner

*Primary Examiner*—Thong Nguyen
(74) *Attorney, Agent, or Firm*—Abelman, Frayne & Schwab

(57) ABSTRACT

A device for an optically controlled micro-manipulation of biological specimens includes at least one micro-manipulator with at least one motor-displaceable cytotechnical instrument holder elements, and a microscope which has at least one functional motor-displaceable element coupled with the motor-displaceable holder in such fashion that, using a control element, a common displacement or adjustment of the holder and a displacement of the at least one functional element of the microscope can be executed in a coordinated fashion so that upon changing a size of a field of view by changing a microscope objective lens, a covered range of displacement of a cytotechnical instrument using the holder is adapted to a new field of view.

5 Claims, 4 Drawing Sheets

DEVICE FOR OPTICALLY CONTROLLED MICRO-MANIPULATION OF BIOLOGICAL SPECIMENS

RELATED APPLICATIONS

This application is a continuation of application Ser. No. 10/484,913 filed Jan. 26, 2004, now abandoned.

BACKGROUND OF THE INVENTION

1. Field of the Invention

The present invention relates to a device for optically controlled micro manipulation of biological specimens. Analogous devices have, as a rule, at least one micro-manipulator, which has at least one motor-displaceable holder for a cytotechnical instrument, with which a biological specimen, primarily a cell or a tissue, can be manipulated.

2. Description of the Prior Art

Cytotechnical instruments are, e.g., capillary tubes or pipettes, with which cells or tissues can be held or manipulated. Typical instruments are holding, etching, biopsy or injection capillary tubes or fine puncturing or cutting instruments or electrodes.

With the motor-displaceable holder, the instrument can be moved in all three spatial axes (xyz-axes) in order to bring its free end into the working position relative to a biological specimen that is to be manipulated.

This type of device mostly comprises two manipulators, each of which has at least one holder for cytotechnical instruments.

In addition, a microscope is provided in this type of devices for optical control of the micro-manipulation operations. Both an inverted or an upright microscope can be used, whereby, in both instances, a transillumination arrangement is conventionally used for examining biological specimens. A number of motor-displaceable functional elements are also provided on the microscope such as, e.g., a microscope table that can be moved or rotated in the xy-direction, a height-displaceable z-drive, a mechanism for changing over the objective lens, etc.

A number of different control elements is provided that make it necessary for the operator to reach around or change position when operating the different functions of the motor-displaceable holder of the micro-manipulator and the displaceable functional elements of the microscope.

DE 19740324.7 discloses providing in a micro-manipulator having two separate holders and a coupling between the two holders. When one of the holders is actuated in a specific fashion by a control element, the other holder automatically executes a preprogrammed, movement that is generally opposite to the movement of the one holder. Thereby, when working with a plurality of instruments, e.g., exchanging instruments is simpler and more reliable.

The object of the invention is to provide a device that can be operated more easily than the known devices.

SUMMARY OF THE INVENTION

In this connection and according to the invention, a device for an optically controlled micro-manipulation of biological specimens includes at least one micro-manipulator with at least one motor-displaceable cytotechnical instrument holder elements, and a microscope which has at least one functional motor-displaceable element coupled with the motor-displaceable holder in such fashion that, by means of a control element, a common displacement or adjustment of the holder and a displacement of the at least one functional element of the microscope can be executed in a coordinated fashion so that upon changing a size of a field of view by changing a microscope objective lens, a covered range of displacement of a cytotechnical instrument using the holder is adapted to a new field of view.

BRIEF DESCRIPTION OF THE DRAWINGS

Below, the invention will be described in detail with reference to the drawings, which show two exemplary embodiments, wherein.

DETAILED DESCRIPTION OF THE PREFERRED EMBODIMENTS

Figure 1A:
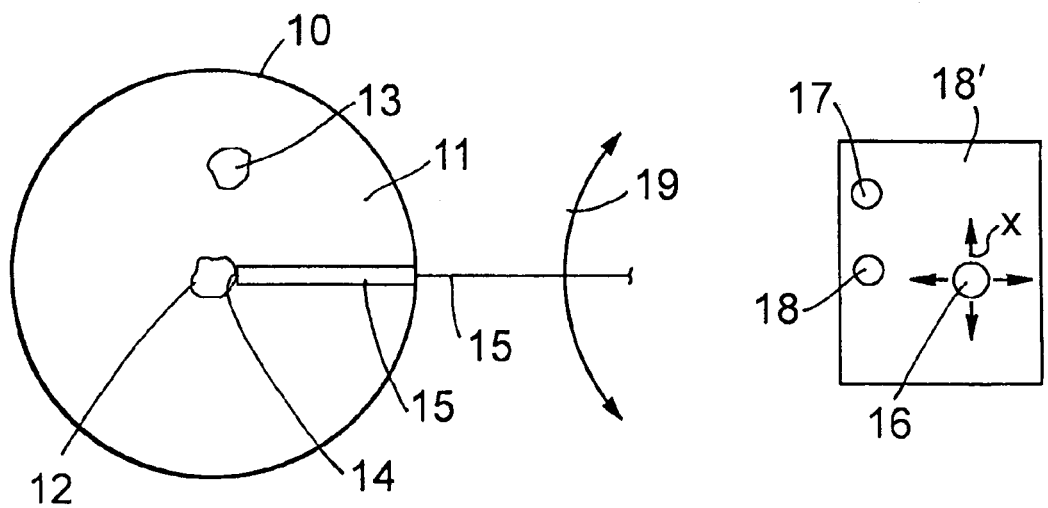
FIG. 1: schematically shows coupling of a joystick-transmission ratio of the manipulator with the objective adjustment of the microscope.

In this connection and according to the invention, at least one function of at least one motor-displaceable holder of the micro-manipulator is coupled to at least one motor-displaceable functional element of the microscope in such a way that both can be actuated in a coordinated manner by a common control element.

The term "activated in a coordinated manner" should be understood to mean that the respective functions of the manipulator and the microscope are expediently coupled by a common control element. The displacement or adjustment of the micro-manipulator and a motor-displaceable functional element of the microscope can accordingly be effected simultaneously or sequentially upon actuating a common control element.

The term "control element" as used in the text below is intended to include all devices that are associated with a function of the manipulator and/or the microscope. If a function of the manipulator and of the microscope is activated in a coordinated manner, then one refers to a common control element. Accordingly, in both cases, e.g., these can be push-buttons or rotary knobs, switches or joysticks, or the like.

Preferably, an operator console is provided, which contains the control elements for the microscope and/or the at least one manipulator. The control elements can easily be connected to a processor, e.g., the processor of the micro-manipulator. A predetermined interface between the processor and the microscope is associated with the processor, so that activation of the functions of the micro-manipulator and of the microscope is essentially restricted according to the invention to a corresponding programming by a common control element, and does not impose any problems or limitations on the hardware.

Within the scope of the invention, therefore, principally all functions of the at least one motor-displaceable drive can be coupled to one or a plurality of the functional elements of the microscope, insofar as this results in a facilitation of the operation.

A particularly preferred embodiment relates to the coupling of the covered range of movement of the cytotechnical instrument, which is effected with a holder, with the field of view obtained with the selected objective.

The field of view, that is, the respective work surface observed using the microscope, e.g., the surface of a Petri dish, decreases with increasing magnification. In order to insure that when processing cells, the instrument movable by of the micro-manipulator does not leave the field of view, its permissible range of movement must accordingly be adapted to the field of view.

In this connection, therefore, provision is made that when displacing the objective lens by a common control element, adaptation of the covered range of movement of the cytotechnical instrument by the holder to the new magnification or the corresponding covered field of view is made.

As a rule, for moving the motor-displaceable holder, a control element displaceable in one or a plurality of spatial axes. e.g. a joystick, is provided. The joystick can, by means of different transmission ratios, control the movement of the instrument in the xy-direction or in many cases in the z-direction, as well.

Accordingly, in the case of the discussed preferred embodiment, upon actuation of a common control element, the objective is changed on the microscope and. e.g., the covered range of movement of the cytotechnical instrument using the joystick is adapted to the new field of view. The transmission ratio of the joystick is advantageously adapted so that regardless of the magnification, upon corresponding movement of the joystick. the cytotechnical instrument, that is, its observed tip, executes a substantially consistent appearing movement within the field of view. The common control element can, if ergonomically possible, be integrated in the joystick, if appropriate. As a rule, however, it is a separate control element.

According to a further advantageous embodiment, provision is made that together with focusing the microscope objective, a corresponding movement of the instrument or its free end is made in the z-direction. This is particularly important. e.g., when the microscope table is shifted together with the Petri dish on it. e.g., in order to change the to-be-processed cell. In this case, it is advantageous if the free end of the instrument can be set as quickly as possible and with minimal control involvement to the optimal position relative to the z-axis for processing the new cell.

This is necessary because, as a rule, the surface of Petri dishes is not flat or the cells lie in different planes. The to-be-processed new cell is, therefore, generally neither in the focus of the microscope objective nor in the correct position relative to the end of the instrument. In this preferred embodiment, it is proposed that upon actuation of a control element for focusing the microscope on the new cell, the position of the instrument relative to the z-axis is correspondingly changed in a coordinated manner, so that upon fine adjustment of the cell, the end of the instrument is again at the optimum processing height (position in the direction of the z-axis) relative to the cell.

According to a further advantageous embodiment, provision is made that upon moving the microscope table, a corresponding positioning of the at least one cytotechnical instrument is effected by a common control element. This is always of interest when, by positioning the microscope table, the position of a cell in the field of view of the microscope is to be changed and the cell is in processing engagement with one or a plurality of cytotechnical instruments. In this case, the instruments must be re-positioned relative to the positioning of the microscope table in order to remain in processing engagement with the cell or in order to re-establish the processing engagement. In this embodiment, upon actuation of a common control element, the required re-positioning of the instrument(s) is made in a coordinated manner with the positioning of the microscope table, which represents a considerable facilitation of operation.

The invention is not limited to the above-discussed embodiments. A number of other possibilities are conceivable as to how the functions of the micro-manipulator and the individual or multiple functional elements of the microscope can be coupled with each other.

It is, e.g., conceivable to store all relevant data on the microscope and manipulator settings in a specific location in the processor and to recall them again by a control element so that the microscope table moves in a coordinated manner into the stored xy-Position, the microscope objective is selected and correspondingly focused, the manipulators move the held instruments into the corresponding xyz-positions and, if applicable, sets the joystick to the desired transmission ratio. Obviously, also only some selected functions of the mentioned functions can be activated with respect to the stored values.

The invention naturally includes devices that comprise not only one but a plurality of manipulators having a plurality of different instruments. In this connection, an advantageous embodiment provides for the holders of the plurality of manipulators containing in the device to be set or adjusted together by a common control element.

Figure 1B:
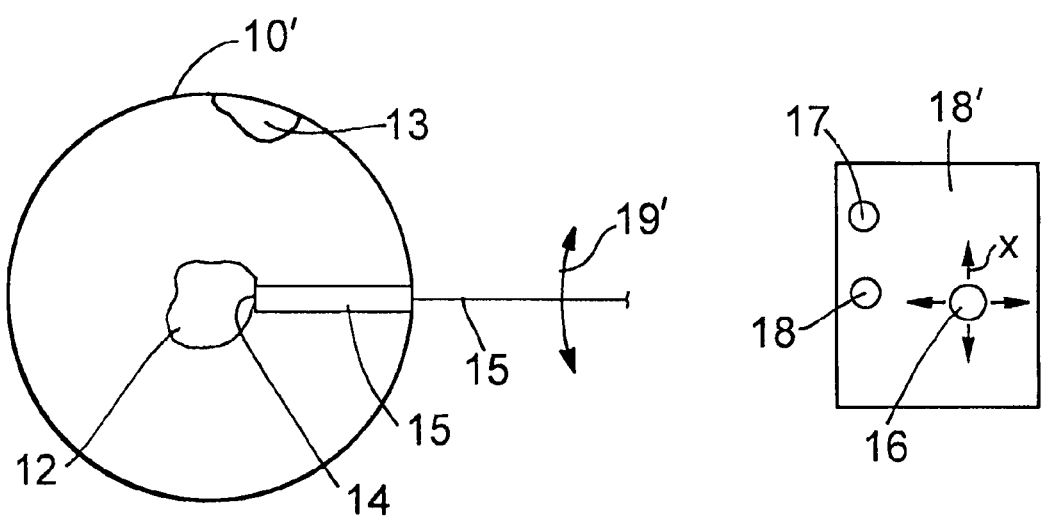

FIG. 1 is broken down into two partial figures a and b, wherein in both cases a field of view 10 or 10' onto a surface 11 of, e.g., a Petri dish [not shown], e.g., containing to-be-processed cells 12, 13.

In the shown example, a cytotechnical instrument 15, which can, e.g., be a capillary tube or a hollow needle, engages operationally the cell 12 with its free end. For the sake of clarity, only a partial view of the instrument is shown. The holder holding the instrument or the manipulator is not shown.

The positioning of the instrument 15 in the xy-direction and, if necessary, also in the z-direction is effected by a control element that can be shifted along the corresponding axes with, e.g., a joystick 16.

The joystick 16 is accommodated along with other control elements 17, 18, in a operator console 18'. The control elements 17, 18 can be assigned arbitrary functions. They can be configured as knobs or switches, etc.

A angular field is shown at 19, 19', respectively, over which the instrument 15 can be moved in the direction of the x-axis with the joystick 16, without leaving the field of view 10 or 10'. Dependent on the set magnification, the angular field 19' is noticeably less than the field 19. The desired angular field can be correspondingly adjusted by changing the transmission of the joystick 16.

According to the invention, the adjustment of the joystick 16 for a specific angular field 19, 19' is effected automatically with the adjustment of the corresponding magnification on the microscope by, e.g., the control element 17 (common control element).

The advantage of the described embodiment consists in that the joystick 16 is automatically offset in time upon actuation of the control element 17 for shifting the objective lens in such a way that at all times movement of the instrument 15 corresponding only to the currently available visual field 10, 10', is possible. In this way, the instrument 15 is prevented from moving outside of the field of view 10, 10'.

In the represented case, the corresponding limitation of the joystick 16 is shown only for the x-axis. Naturally, in practice, the displacement of the y-axis is adapted accordingly. Upon displacement of the instrument 15 in the z-axis, which can be effected by rotation of the joystick 16, e.g., no forced limitation is required.

Figure 2:
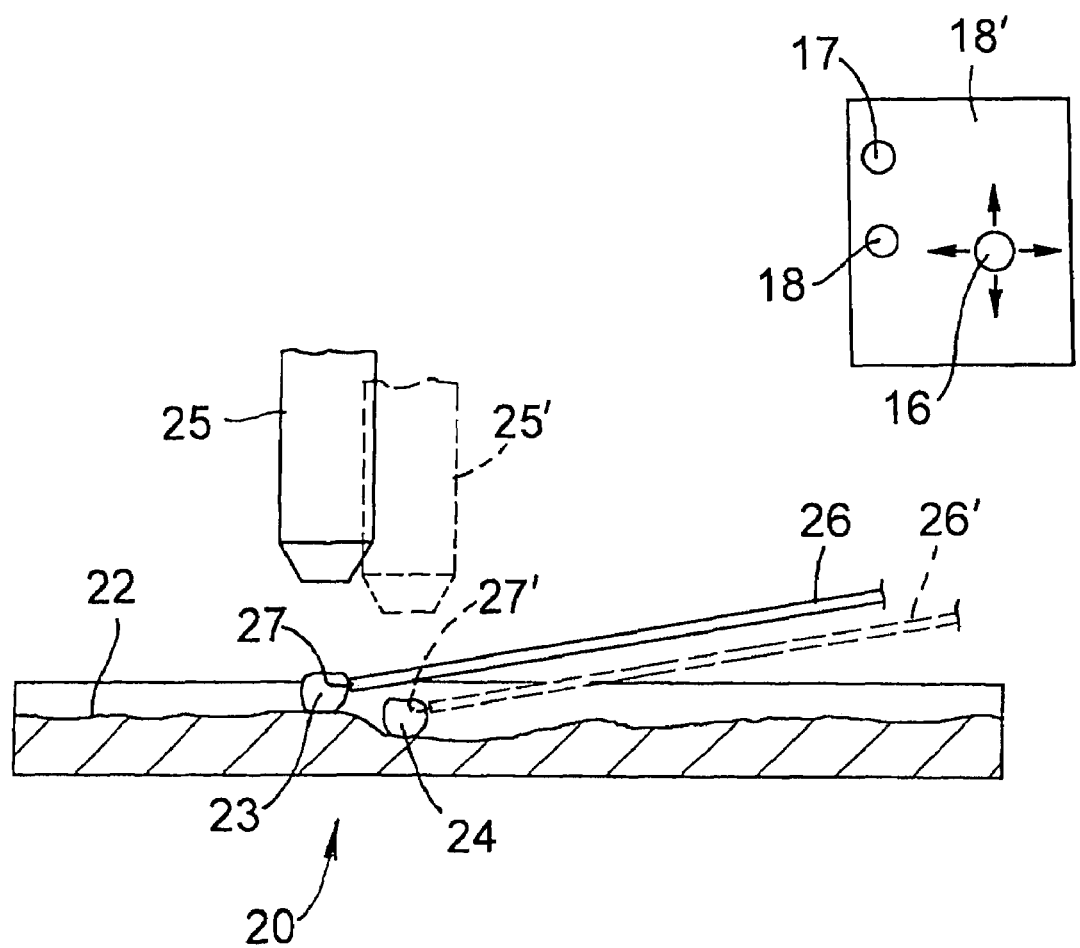
FIG. 2: likewise schematically shows the possible coupling between focusing of the objective and z-position of an instrument.

FIG. 2 shows a lateral view of a Petri dish 20 having a work surface 22, on which the to-be-processed cells 23 and 24 are placed. In addition, the operator console 18' of FIG. 1 is represented with the control elements 16, 17 and 18.

Processing of the cells 23 and 24 is effected under visual control of a microscope [not shown], of which only an objective lens 25, 25' in different focal positions is shown.

Processing of the cells 23 and 24 is effected in the shown case with a cytotechnical instrument 26, 26' shown here in two different positions and the tip 27, 27', of which is in an optimal position of intervention with respect to the cell 23 or 24, respectively.

Because of the work surface 22 of the Petri dish 20 is not flat, the position of the cells 23 and 24 deviates also relative to the z-axis.

With the transition of processing from the cell 23 to the cell 24, re-focusing is necessary and the position of the instrument 26 must be changed in the direction of z-axis so that its tip 27 is again in the optimum position of intervention with the cell 24.

Upon changing the processing over, a possibility exists to correspondingly shift the Petri dish 20 under the objective. There are also microscope tables on which the micro-manipulator is fixedly mounted. The xy-displaceable platform is designed so as to accommodate the microscope, so that the entire microscope can be shifted accordingly.

According to the invention, provision is made that upon focusing the objective 25' on the cell 24, e.g., a corresponding displacement of the instrument 26 in the z-direction occurs automatically. Thus, the identical processing conditions are automatically adjusted as in the case of processing the cell 23.

Actuation of both functions can by done by the control element 18.

Figure 3:
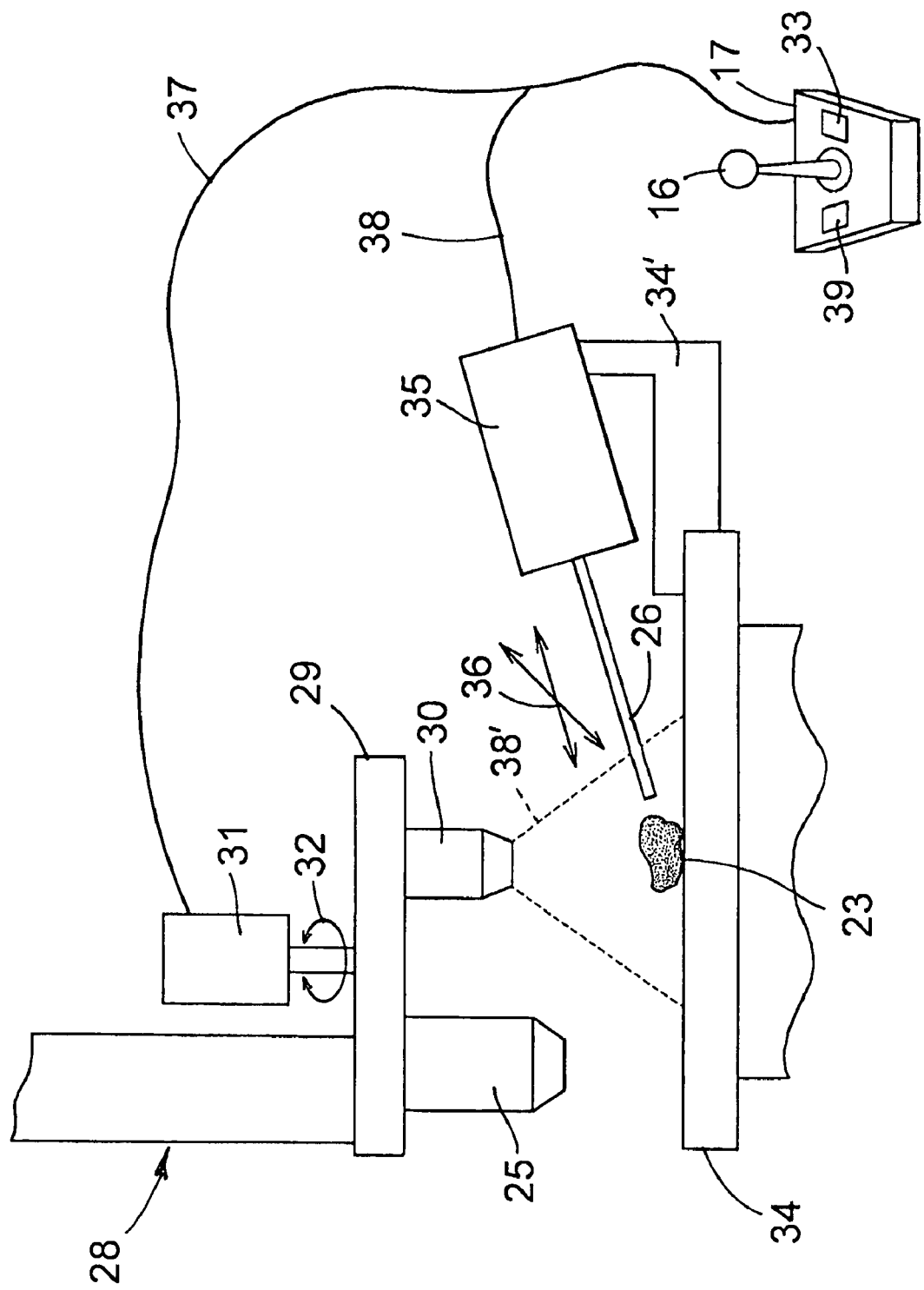
FIG. 3: shows schematically an optically controlled micro-manipulation device according to the present invention.

FIG. 3 represents schematically the optically controlled micro-manipulation device according to the present invention. The device, as it has already been mentioned above, includes a microscope 28 having a turret 29 to which two objective lenses 25 and 30 are secured. A motor 31 rotates the turret 29 in the direction of arrow 32 to provide for substitution of one of lenses 25 and 30 by another lens 25, 30. The motor 31 can be actuated by the control element 17 which is provided to this end, or example, with a pushbutton 33. The microscope 28 has a table 34 for the treatable cell 23. The microscope table 34 is provided with a bracket 34' for supporting a holder 35 of the cytotechnical instrument 26. The holder 35 includes a drive that moves the instrument 26 in the direction of arrows 36. The movement of the instrument 26 is controlled with the joystick 16 of control element 17. Conductors 37 and 38 connect, respectively, the microscope drive 31 and the instrument drive with the control element 17, whereby an operation of at least one functional element of the microscope 28 and of the instrument drive 35 can be coordinated. Thus, upon actuation of the button 33, the microscope motor 31 is actuated, rotating the turret 29, and the objective lens 25 will replace the objective lens 30. Simultaneously with the actuation of the microscope drive 31, the instrument drive is also actuated to adapt the range of movement of the instrument 26 to the new field of vision.

Figure 4:
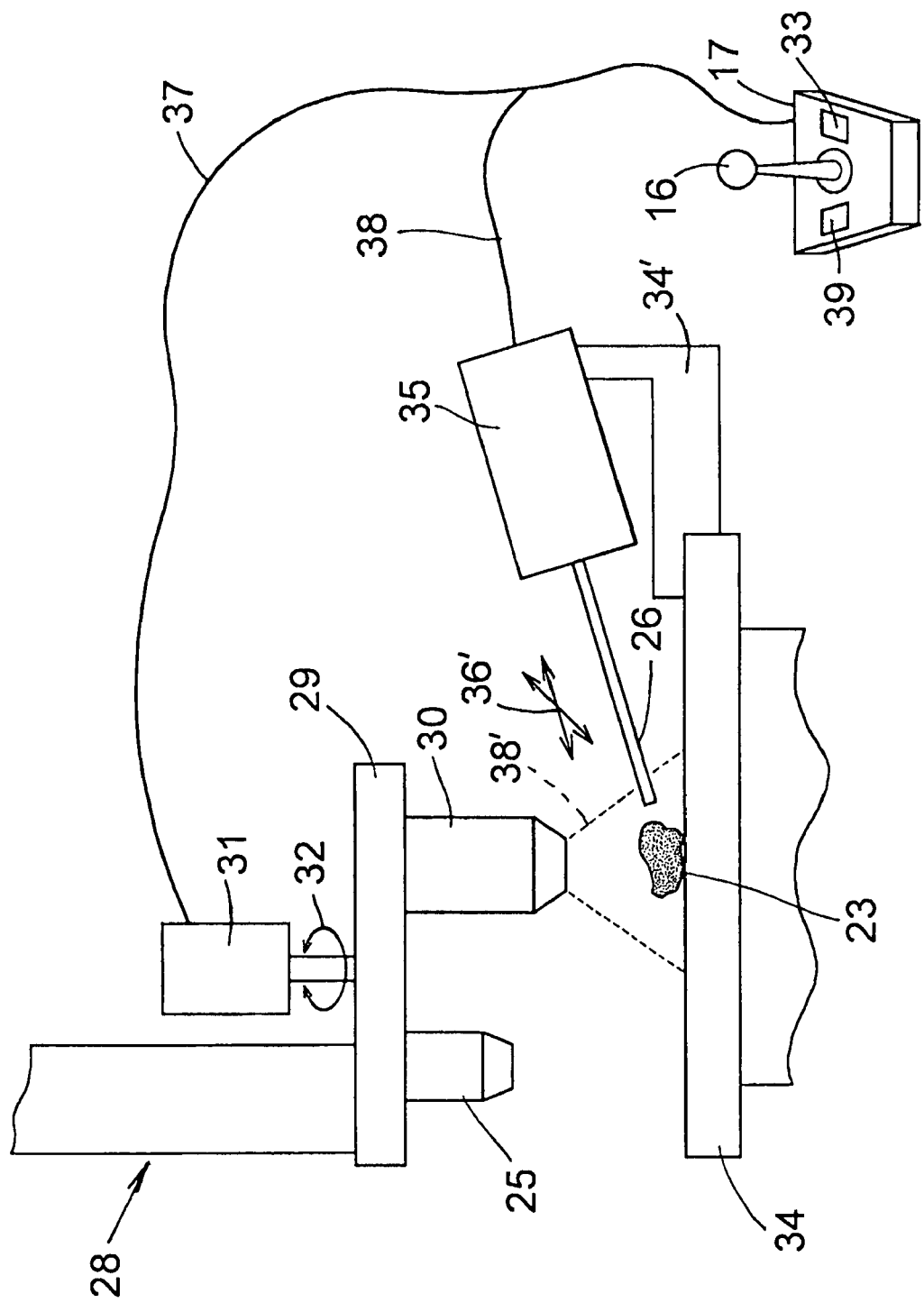
FIG. 4: shows the device shown in FIG. 3 in a position with a different field of vision than that in FIG. 3.

The new position of the turret 29 is shown in FIG. 4, in this position, the field of vision 38' is smaller than in the position shown in FIG. 3. Also is decreased the range of movement of the instrument 26, as shown with arrows 36' in FIG. 4, which are shown as being shorter than arrows 36 in FIG. 3. A further button 39 provided on the control element 17 provides for further adjustments of the microscope 28, for example, for displacing the microscope table 34, together with the displacement of the instrument 26.

Though the present invention was shown and described with references to the preferred embodiments, such are merely illustrative of the present invention and are not to be construed as a limitation thereof and various modifications of the present invention will be apparent to those skilled in the art. It is, therefore, not intended that the present invention be limited to the disclosed embodiments or details thereof, and the present invention includes all variations and/or alternative embodiments within the spirit and scope of the present invention as defined by the appended claims.

What is claimed is:

1. A device for an optically controlled micro-manipulation of a biological specimen, including a cell of interest, the device comprising:
    at least one micro-manipulator including:
        a cytotechnical instrument including a capillary with a tip; and
        a cytotechnical instrument holder having a drive for displacing the holder together with the cytotechnical instrument;
    a microscope having:
        at least one functional element with a plurality of objective lenses having, respectively, fields of view with different sizes, and
        a motor for displacing the functional element in order to obtain a field of view of a different size;
    manually operated means for displacing the holder together with the cytotechnical instrument over a range of movement of the cytotechnical instrument corresponding to a field of view of the microscope; and
    a common control element for controlling respective operations of both the cytotechnical instrument-displacing drive and the functional element-displacing motor in coordinated fashion,
    wherein upon changing of a size of a selected field of view by actuation of the control element, the manually operated means is automatically adjusted to provide a displacement of the holder together with the cytotechnical instrument over a new range of movement of the cytotechnical instrument corresponding to a changed size of the selected field of view of the microscope, thereby localizing the cell of interest in a cell culture under optical control and positioning the tip of the capillary in the selected field of view for an injection from the capillary to the cell of interest.

2. The device according to claim 1, wherein in order to adapt a covered range of movement of the cytotechnical instrument using the holder to the new size of the field of view, a transmission ratio of the manually operated means controlling the holder is correspondingly changed.

3. The device according to claim 1, wherein upon displacement of a microscope table or the microscope by actuation of the control element a corresponding displacement of the holder, together with the cytotechnical instrument, takes place.

4. The device according to claim 1, wherein specific stored settings of one or a plurality of motor-displaceable functional elements of the microscope and of the motor-displaceable holder are refined and readjusted by actuation of the control element.

5. The device according to claim 1, wherein the common control element is provided on an operator console.

* * * * *